United States Patent [19]

Reynders

[11] Patent Number: 5,356,471

[45] Date of Patent: Oct. 18, 1994

[54] PIGMENTS OF DARK SURFACE COLOR

[75] Inventor: Peter Reynders, Griesheim, Fed. Rep. of Germany

[73] Assignee: Merck Patent Gesellschaft mit Beschrankter Haftung, Darmstadt, Fed. Rep. of Germany

[21] Appl. No.: 107,183

[22] Filed: Aug. 17, 1993

[30] Foreign Application Priority Data

Aug. 17, 1992 [DE] Fed. Rep. of Germany ....... 4227082

[51] Int. Cl.⁵ .............................................. C04B 14/04
[52] U.S. Cl. .................................... 106/489; 106/490; 106/415
[58] Field of Search ............... 106/415, 417, 472, 475, 106/481, 489, 490, 474

[56] References Cited

U.S. PATENT DOCUMENTS

| | | | |
|---|---|---|---|
| Re. 30,450 | 12/1980 | Iannicelli | 106/475 |
| 3,094,428 | 6/1963 | Hamilton et al. | 106/475 X |
| 3,107,173 | 10/1963 | Klenke | 106/479 |
| 4,076,551 | 2/1978 | Bernhard et al. | 106/474 X |
| 5,271,771 | 12/1993 | Franz et al. | 106/474 |

*Primary Examiner*—Karl Group
*Assistant Examiner*—Chris Gallo
*Attorney, Agent, or Firm*—Millen, White, Zelano & Branigan

[57] ABSTRACT

The present invention relates to platelet-like pigments of dark surface color and to their preparation process and use.

13 Claims, No Drawings

PIGMENTS OF DARK SURFACE COLOR

BACKGROUND OF THE INVENTION

The invention relates to pigments based on platelet-like (i.e., plate-shaped) substrates and having a dark, in particular black, surface color and to their preparation process and use.

Colored platelet-like substrates, such as, for example, metals, metal oxides or platelet-like substrates coated with metal oxides, are used in many technical fields. Although it is possible to produce a large number of hues by means of known processes, there is a need for pigments having interesting new colors and property profiles not only for applications in cosmetics but also in industry.

Pigments of dark, in particular black, surface color are obtainable, for example, by incorporation of carbon black in pigments, resulting in pigments having special color effects. However, the known processes for preparing black pigments have in part substantial disadvantages. A further disadvantage is the frequently observable bleeding of the carbon black upon suspension of the pigments in organic solvents for producing coating systems and the instability at elevated temperatures.

SUMMARY OF THE INVENTION

Accordingly, there was a need for a simple process for preparing pigments of dark surface color which do not have any of the disadvantages mentioned. This object is achieved by the present invention.

Surprisingly, it has been found that temperature-stable pigments of black surface color having a high luster are obtained by reacting platelet-like substrates with a silane followed by pyrolysis, e.g., at temperatures of preferably more than 700° C. in non-oxidizing, preferably inert, gas atmosphere.

This process leads to the formation on the pigment surface of a layer comprising black $SiO_2$ glass that contains silicon oxycarbide and/or carbon black.

Accordingly, the invention relates to platelet-like pigments of dark surface color, characterized in that a platelet-like substrate is covered with an $SiO_2$ layer containing silicon oxycarbide and/or carbon black.

The invention also relates to a process for preparing pigments of dark surface color, characterized in that an aqueous suspension of a platelet-like substrate is reacted with a silane and then calcined in a non-oxidizing, e.g., preferably inert, atmosphere. Such atmospheres may include nitrogen, argon or helium, in addition to other gases, in proportions which do not result in oxidation of the substrate and silane.

According to the process according to the invention, virtually all substrates which are stable at temperatures above, e.g., 700° C. can be used. Advantageously, they should be present in finely divided form, i.e. in particle sizes of between about 0.5 and 1000 μm.

Preferably, the substrates used are metal oxide platelets and platelet-like materials coated with metal oxides. Platelet-like iron oxide and mica platelets (muscovite, phlogopite, synthetic mica) coated with metal oxides or basic aluminum sulphate are particularly suitable. The latter pigments, known as pearl luster pigments, are disclosed, for example, in German Patents and Patent Applications 1,467,568, 1,959,998, 2,009,56, 2,214,545, 2,215,191, 2,244,298, 2,313,331, 2,522,572, 3,137,808, 3,137,809, 3,151,343, 3,151,354, 3,151,355, 3,211,602 and 3,235,017.

Any silanes known to one skilled in the art can be used for coating the substrates. Preferred compounds are of the formula I

$SiX_nR_m$ in which
X is a hydrolyzable group, preferably alkoxy having 1–10 C atoms or halogen,
R is an alkyl group having 1–30 C atoms, in which one or two non-adjacent $CH_2$ groups can also be replaced by —O—, —CO—, —COO—, —OCO— or —HC=CH—, or is Ar—Y—$(CH_2)_x$—, in which
Ar is a phenyl radical in which one or two CH groups can be replaced by N,
Y is —O—, —S—, —NH— or a single bond, and
x is 0–5,
n and m are 1, 2 or 3, n+m being 4.

Preferred silanes of the formula I are ternary compounds of the formula $SiX_3R$ in which R is an alkyl or phenyl group of the formula Ar—Y—$(CH_2)_x$ and X is an alkoxy group having 1–3 C atoms, more preferably methoxy or ethoxy, or chlorine.

Particularly preferred silanes of the formula I are phenyltrimethoxysilane, methacryloxypropyltrimethoxysilane, N-phenylaminopropyltrimethoxysilane, phenylalkyltrimethoxysilane, having 1–20 C atoms, such as, for example, phenylethyltrimethoxysilane, phenylpropyltrimethoxysilane, phenylpentyltrimethoxysilane, phenyldecyltrimethoxysilane, phenyldodecyltrimethoxysilane, phenyloctadecyltrimethoxysilane. An amount of about 0.002–50 % by weight, relative to the entire pigment, preferably 0.005–15 % by weight, has proven to be useful, the amount of silane used depending not only on the substrate but also on the desired surface color. The end products then contain the amounts of silicon oxycarbide and/or carbon black-containing $SiO_2$ glass corresponding to the molar amount of silane used. The coatings layer may contain a mixture of $SiO_2$, SiC, C, silicon oxycarbide and polycarbosilane pyrolysis products, in proportions that do not affect the properties of the pigments.

Depending on the amount of silane used, pigments of grey or black surface color are obtained. When grey pigments are prepared, about 0.005–3 % by weight of silane, in particular 0.05–2 % by weight, are preferably used. Preferably, silanes having a saturated or unsaturated aliphatic chain are used, while in the case of black pigments preferably silanes having an aromatic radical are used. The larger the amount of silane used, the darker the pigment color of the silanized pigment. In the case of pigments of black surface color, the amount of silane used is about 3–15 % by weight, relative to the entire pigment.

Coating of the substrates is carried out by suspending them in water, bringing the pH to a suitable value!, and adding the silane compound, preferably dissolved in a 90–100 % alcohol, preferably ethanol, directly to the pigment suspension. This results in prehydrolysis of the silane compound. The process even takes place at low temperatures, for example at 20° to 90° C., preferably 70° to 80° C.

The hydrolyzate is chemically or physically adsorbed on the substrate surface. The adhesive strength or the adsorption is determined by the substrate surface. The substrates should have a hydrophilic surface containing hydroxyl groups.

The reaction mixture is then heated, brought to a pH of >8 with a base, and stirred for another 24-48 hours.

The pH values in the process depend on the silane compound used, the substrate surface and the ratios of concentration. Advantageously, industrially easily available bases such as NaOH, KOH or ammonia, are used for adjusting the pH, and the acids used are dilute mineral acids, for example HCl or $H_2SO_4$. Since the bases and acids are only used for changing the pH, their nature is uncritical, so that other bases and acids can also be used.

In the last step, the coated pigments are filtered off, washed, dried and calcined in a substantially inert gas atmosphere at a temperature effective to support pyrolysis, preferably at temperatures above about 700° C. By "substantially inert" is meant an atmosphere in which oxidation does not occur to an extent which would detrimentally affect the products. Under pyrolytic conditions, the layer adhering to the substrate surface is converted into the $SiO_2$ layer containing carbon black and/or into the silicon oxycarbide glass. Pyrolysis preferably takes place at temperatures of between about 700° and 1000° C., but can also be carried out at higher temperatures. The duration is about 0.1 to 24 h, preferably 0.5 to 1 h.

Depending on the amount of silicon oxycarbide layer or SiO2 layer containing carbon black present, the pigment has a grey to black surface color.

In particular black pigments based on platelet-like $TiO_2$ interference pigments are distinguished by their high color intensity.

The pigments prepared according to the invention have a dark surface color, are wear-resistant and temperature-stable and have high luster, enabling them to be used for a wide range of purposes, in particular in thermoplastic materials and automotive baking finishes.

Accordingly, the invention also relates to the use of the pigments according to the invention in formulations such as paints, varnishes, dyes, plastics and cosmetics.

In the foregoing and in the following examples, all temperatures are set forth uncorrected in degrees Celsius; and, unless otherwise indicated, all parts and percentages are be weight.

The entire disclosure of all applications, patents and publications, cited above and below, and of corresponding German application No. P 42 27 082.0, filed Aug. 17, 1992, is hereby incorporated by reference.

EXAMPLES

EXAMPLE 1

50 g of mica (muscovite of particle size 10-60 μm) are suspended in 500 ml of fully deionized water. The pH of the suspension is brought to 3 with 1N Cl. After addition of the silane solution (5.0 g of phenylethyltrimethoxysilane in 25 ml of 96 % ethanol), the mixture is heated to 70° C. and the pH is brought to 8 with aqueous ammonium hydroxide solution. After stirring at room temperature for another 24 h, the coated mica pigment is filtered off, washed with fully deionized water until salt-free, and the pigment is dried at 140° C. for 12 h. The dried pigment is calcined at 900° C. in an N2 stream for 45 minutes, giving a pigment of dark, lustrous surface color.

EXAMPLE 2

50 g of Iriodin 103 (TiO2-coated mica pigment of particle size 10-50 μm from E. Merck, Darmstadt) are coated analogously to Example 1 with methacryloxypropyltrimethoxysilane (5.0 g of silane in 25 ml of 96 % ethanol). Pyrolysis at 900° C. in an $N_2$ stream gives a pigment of black surface color.

EXAMPLE 3

50 g of Iriodin 225 (TiO2-coated mica pigment of particle size 10-60 μm from E. Merck, Darmstadt) are suspended in 500 ml of fully deionized water. The pH of the suspension is brought to 3 with 1N HCl. A solution consisting of 1.6 g of N-phenylaminopropyltrimethoxysilane in 50 ml of 96% ethanol is added to the pigment suspension. The mixture is heated to 85° C., and the pH is brought to 8 with aqueous ammonium hydroxide solution. After stirring at room temperature for 24 hours, the pigment is filtered off, washed and dried at 120° C. for 12 h. The dried pigment is calcined at 900° C. in an N2 stream for 45 minutes, giving a pigment of black surface color and an intensive blue interference color.

EXAMPLE 4

50 g of Iriodin 504 (mica pigment of particle size 10-60 μm coated with iron(III) oxide from E. Merck, Darmstadt) are treated analogously to Example 3 with a 3-methacryloxypropyltrimethoxysilane solution (1.6 g of silane in 50 mi of 96% ethanol), giving a magnetic red-brown pigment of black surface color.

EXAMPLE 5

125 g of Iriodin 111 (TiO2-coated mica pigment of particle size<15 μm from E. Merck, Darmstadt) are suspended in 500 ml of fully deionized water. The mixture is heated to 75° C., and the pH is brought to 5.6 with 1N HCl. A solution consisting of 2.5 g of n-octadecyltrimethoxysilane in 100 ml of 96% ethanol is added in portions to the pigment suspension. After stirring for 0.5 h, the pigment is filtered off and washed until salt-free. The pigment dried at 140° C. is finally calcined at 850° C. in an N2 stream for 0.5 h, giving a silver-grey pigment of high luster.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A platelet-shaped pigment, comprising a platelet-shaped substrate having a coating layer comprising silicon oxycarbide glass.

2. A pigment according to claim 1, wherein the coating amounts to 0.002 to 50% by weight of the entire pigment.

3. A process for the preparation of a pigment, comprising reacting an aqueous suspension of a platelet-shaped substrate with a silane and calcining said substrate in a non-oxidizing atmosphere.

4. A process according to claim 3, wherein pyrolysis is effected.

5. A process according to claim 4, wherein the pigment prepared is a platelet-shaped substrate having a coating layer comprising silicon oxycarbide glass.

6. A process according to claim 3, wherein the silane is added to the substrate suspension at an acidic pH, and the pH is then raised to effect precipitation of the silane on the substrate.

7. A process according to claim 3, wherein the silane has the formula I $$SiX_nR_m \qquad\qquad I$$

in which
- X is a hydrolyzable group, preferably alkoxy having 1–10 C atoms or halogen,
- R is an alkyl group having 1–30 C atoms, in which one or two non-adjacent $CH_2$ groups can also be replaced by —O—, —CO—, —COO—, —OCO— or —HC=CH—, or is Ar—Y—$(CH_2)_x$—, in which
- Ar is a phenyl radical in which one or two CH groups can be replaced by N,
- Y is —O—, —S—, —NH— or a single bond, and
- x is 0–5,
- n and m are 1, 2 or 3, n+m is 4.

8. A process according to claim 7, wherein X is $C_{1-10}$-alkoxy or halogen.

9. A process according to claim 7, wherein the silane is $SiX_3R$, in which X is $C_{1-3}$-alkoxy and R is Ar—Y—$(CH_2)_x$.

10. A process according to claim 7, wherein the amount of the silane is 0.005–3 % by weight, relative to the entire pigment.

11. A process according to claim 7, wherein the amount of the silane is 0.002–0.50% by weight, relative to the entire pigment.

12. A pigment produced by a process according to claim 3.

13. A pigment produced by a process according to claim 7.

* * * * *